(12) United States Patent
Castillo et al.

(10) Patent No.: US 7,402,609 B2
(45) Date of Patent: *Jul. 22, 2008

(54) OLOPATADINE FORMULATIONS FOR TOPICAL ADMINISTRATION

(75) Inventors: Ernesto J. Castillo, Arlington, TX (US); Wesley Wehsin Han, Arlington, TX (US); Huixiang Zhang, Fort Worth, TX (US); Haresh G. Bhagat, Fort Worth, TX (US); Onkar N. Singh, Arlington, TX (US); Joseph Paul Bullock, Fort Worth, TX (US); Suresh C. Dixit, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/079,996

(22) Filed: Mar. 15, 2005

(65) Prior Publication Data

US 2005/0158387 A1 Jul. 21, 2005

Related U.S. Application Data

(63) Continuation of application No. 10/175,106, filed on Jun. 19, 2002, now Pat. No. 6,995,186.

(60) Provisional application No. 60/301,315, filed on Jun. 27, 2001.

(51) Int. Cl.
*A61K 31/333* (2006.01)

(52) U.S. Cl. .................................................. 514/450

(58) Field of Classification Search ....................... None
See application file for complete search history.

(56) References Cited

U.S. PATENT DOCUMENTS

| | | | | |
|---|---|---|---|---|
| 4,407,791 | A | 10/1983 | Stark | 424/80 |
| 4,749,700 | A | 6/1988 | Wenig | 514/225.2 |
| 4,871,865 | A | 10/1989 | Lever, Jr. et al. | 549/354 |
| 4,923,892 | A | 5/1990 | Lever, Jr. et al. | 514/450 |
| 5,116,863 | A | 5/1992 | Oshima et al. | 514/450 |
| 5,164,194 | A | 11/1992 | Hettche | 424/489 |
| 5,641,805 | A | 6/1997 | Hayakawa et al. | 514/450 |
| 6,146,622 | A | 11/2000 | Castillo et al. | 424/78.02 |
| 6,174,914 | B1 | 1/2001 | Yanni et al. | 514/450 |
| 6,207,684 | B1 | 3/2001 | Aberg | 514/324 |
| 6,274,626 | B1 * | 8/2001 | Jonasse et al. | 514/568 |
| 6,316,483 | B1 | 11/2001 | Hasiwanter et al. | 514/401 |
| 6,333,044 | B1 | 12/2001 | Santus et al. | 424/434 |
| 2001/0056093 | A1 | 12/2001 | Yanni | 514/218 |

FOREIGN PATENT DOCUMENTS

| | | |
|---|---|---|
| EP | 0 048 023 | 3/1982 |
| EP | 0 214 779 | 3/1987 |
| EP | 0 235 796 | 9/1987 |
| JP | 61926 | 3/1995 |
| WO | WO 00/03705 | 1/2000 |
| WO | WO 01/21209 | 3/2001 |
| WO | WO 01/21210 | 3/2001 |
| WO | WO 01/35963 | 5/2001 |
| WO | WO 01/54687 A1 | 8/2001 |
| WO | WO 91/54687 A1 | 8/2001 |
| WO | WO 02/30395 A1 | 4/2002 |
| WO | WO 03/002093 | 1/2003 |
| WO | WO 2004/043470 | 5/2004 |

OTHER PUBLICATIONS

Church, "Is Inhibition of Mast Cell Mediator Release Relevant to the Clinical Activity of Anti-allergic Drugs?," *Agents and Actions*, vol. 18, ¾, pp. 288-293 (1986).

Clegg et al., "Histamine Secretion from Human Skin Slices Induced by Anti-IgE and Artificial Secretagogues and the Effects of Sodium Cromoglycate and Salbutanol," *Clin. Allergy*, vol. 15, pp. 321-328 (1985).

Hamilton et al., "Comarison of a New Antihistaminic and Antiallergic Compound KW 46790 with Terfenadine and Placebo on Skin and Nasal Provocation in Atopic Individuals," *Clinical and Experimental Allergy*, vol. 24, pp. 955-959 91994).

Ikeda et al., "Effects of Oxatomide and KW-4679 on Acetylcholine-Induced Responses in the Isolated Acini of Guinea Pig Nasal Glands," *Int. Arch. Allergy Immunol.*, vol. 106, p. 157-162 (1995).

Irani et al., "Mast Cell Heterogeneity," *Clinical and Experimental Allergy*, vol. 19, pp. 143-155 (1989).

Kamei et al., "Effects of Certain Antiallergic Drugs on Experimental Conjunctivitis in Guinea Pigs," *Atarashii Ganka*, vol. 11(4), p. 603-605 (1994) (abstract only).

(Continued)

*Primary Examiner*—Zohreh A Fay
(74) *Attorney, Agent, or Firm*—Patrick M. Ryan

(57) ABSTRACT

Topical formulations of olopatadine for treatment of allergic or inflammatory disorders of the eye and nose are disclosed. The aqueous formulations contain approximately 0.17-0.62% (w/v) of olopatadine and an amount of polyvinylpyrrolidone or polystyrene sulfonic acid sufficient to enhance the physical stability of the formulations.

1 Claim, No Drawings

OTHER PUBLICATIONS

Kamei et al., "Effect of (Z)-11-[3-(Dimethylamino) propylidene]-6,11-dihydrodibenz[b,e]oxepin-2-acetic Acid Hydrochloride on Experimental Allergic Conjunctivitis and Rhinitis in Rats and Guinea Pigs," *Arzneimittelforschung*, vol. 45(9), p. 1005-1008 (1995).

Ohshima et al., "Synthesis and Antiallergic Activity of 11-(Aminoalkylidene)-6,11,dihydrodibenz[b,e]oxepin Derivatives," *J. Medicinal Chemistry*, vol. 35(11), p. 2074-2084 (1992).

Pearce et al., "Effect of Disodium Cromoglycate on Antigen Evoked Histamine Release in Human Skin," *Clinical Exp. Immunol.*, vol. 17, pp. 437-440 (1974).

Sharif et al., "Characterization of the Ocular Antiallergic and Antihistaminic Effects of Olopatadine (AL-4943A), a Novel Drug for Treating Ocular Allergic Diseases," *J. of Pharmacology and Experimental Therapeuticsl*, vol. 278(3), p. 1252-1261 (1996).

Sharif et al., "Olopatadine (AL-4943A): Pharmacological Profile of a Novel Anti-histaminic/Anti-allergic Drug for Use in Allergic Conjunctivitis," *Investigative Ophthalmology & Visual Science*, vol. 37(3), p. 1027 (1996) (abstract only).

Siraganian, "An Automated Continuous Flow System for the Extraction and Fluorometric Analysis of Histamine," *Anal. Biochem.*, vol. 57, pp. 383-394 (1974).

Spitalny et al., "Olopatadine Ophthalmic Solution Decreases Itching and Redness Associated with Allergic Conjunctivitis," *Investigative Ophthalmology & Visual Science*, vol. 37(3), p. 593 (1996) (abstract only).

"The Lung," *Scientific Foundation*, Raven Press, Ltd., New York, Ch. 3.4.11 (1991).

Yanni et al., "The In Vitro and In Vivo Ocular Pharmacology of Olopatadine (AL-4943A), An Effective Anti-allergic/Anti-histaminic Agent," *Investigative Ophthalmology & Visual Science*, vol. 37(3), p. 1028 (1996) (abstract only).

Zhang et al., "Optically Active Analogues of Ebastine: Synthesis and Effect of Chirality on Their Antihistaminic and Antimuscarinic Activity," *Chirality*, vol. 6(8), p. 631-641 (1994).

Astelin® Nasal Spray Product Insert.

* cited by examiner

OLOPATADINE FORMULATIONS FOR TOPICAL ADMINISTRATION

This application is a continuation application of U.S. Ser. No. 10/175,106, filed June 19, 2002 now U.S. Pat. No. 6,995,186.

This application claims priority to U.S. Provisional Application, Ser. No. 60/301,315, filed Jun. 27, 2001.

BACKGROUND OF THE INVENTION

1. Field of the Invention

The present invention relates to topical formulations used for treating allergic and inflammatory diseases. More particularly, the present invention relates to formulations of olopatadine and their use for treating and/or preventing allergic or inflammatory disorders of the eye and nose.

2. Description of the Related Art

As taught in U.S. Pat. Nos. 4,871,865 and 4,923,892, both assigned to Burroughs Wellcome Co. ("the Burroughs Wellcome Patents"), certain carboxylic acid derivatives of doxepin, including olopatadine (chemical name: Z-11-(3-dimethylaminopropylidene)-6,11-dihydrodibenz[b,e]oxepine-2-acetic acid), have antihistamine and antiasthmatic activity. These two patents classify the carboxylic acid derivatives of doxepin as mast cell stabilizers with antihistaminic action because they are believed to inhibit the release of autacoids (i.e., histamine, serotonin, and the like) from mast cells and to inhibit directly histamine's effects on target tissues. The Burroughs Wellcome Patents teach various pharmaceutical formulations containing the carboxylic acid derivatives of doxepin, including nasal spray and ophthalmic formulations. See, for example, Col. 7, lines 7-26, and Examples 8 (H) and 8 (I) of the '865 patent.

U.S. Pat. No. 5,116,863, assigned to Kyowa Hakko Kogyo Co., Ltd., ("the Kyowa patent"), teaches that acetic acid derivatives of doxepin and, in particular, olopatadine, have anti-allergic and anti-inflammatory activity. Olopatadine is the cis form of the compound having the formula:

Medicament forms taught by the Kyowa patent for the acetic acid derivatives of doxepin include a wide range of acceptable carriers; however, only oral and injection administration forms are mentioned.

U.S. Pat. No. 5,641,805, assigned to Alcon Laboratories, Inc. and Kyowa Hakko Kogyo Co., Ltd., teaches topical ophthalmic formulations containing olopatadine for treating allergic eye diseases. According to the '805 patent, the topical formulations may be solutions, suspensions or gels. The formulations contain olopatadine, an isotonic agent, and "if required, a preservative, a buffering agent, a stabilizer, a viscous vehicle and the like." See Col. 6, lines 30-43. "[P]olyvinyl alcohol, polyvinylpyrrolidone, polyacrylic acid or the like" are mentioned as the viscous vehicle. See Col. 6, lines 55-57.

PATANOL® (olopatadine hydrochloride ophthalmic solution) 0.1% is currently the only commercially available olopatadine product for ophthalmic use. According to its labelling information, it contains olopatadine hydrochloride equivalent to 0.1% olopatadine, 0.01% benzalkonium chloride, and unspecified amounts of sodium chloride, dibasic sodium phosphate, hydrochloric acid and/or sodium hydroxide (to adjust pH) and purified water. It does not contain polyvinyl alcohol, polyvinylpyrrolidone, polyacrylic acid or any other polymeric ingredient.

Topical olopatadine formulations that have prolonged therapeutic activity and are effective as products for treating allergic or inflammatory conditions in the eye and nose are desirable. Topical olopatadine formulations that are effective as once-a-day products for treating allergic conditions in the eye are desirable.

SUMMARY OF THE INVENTION

The present invention provides topical olopatadine formulations that are effective as once-a-day products for treating allergic or inflammatory disorders of the eye and are effective for treating allergic or inflammatory disorders of the nose. The formulations of the present invention are aqueous solutions that comprise approximately 0.2-0.6% olopatadine. In addition to their relatively high concentration of olopatadine, they also contain an amount of polyvinylpyrrolidone or polystyrene sulfonic acid sufficient to enhance the physical stability of the solutions.

Among other factors, the present invention is based on the finding that polyvinylpryrrolidone and polystyrene sulfonic acid, unlike polyvinyl alcohol and the polyacrylic acid carbomer 974P, enhance the physical stability of solutions containing approximately 0.2-0.6% olopatadine.

DETAILED DESCRIPTION OF THE INVENTION

Unless indicated otherwise, all component amounts are presented on a % (w/v) basis and all references to olopatadine are to olopatadine free base.

Olopatadine is a known compound that can be obtained by the methods disclosed in U.S. Pat. No. 5,116,863, the entire contents of which are hereby incorporated by reference in the present specification. The solution formulations of the present invention contain 0.17-0.62% olopatadine. Preferably, the solution formulations intended for use in the eye contain 0.17-0.25% olopatadine, and most preferably 0.18-0.22% olopatadine. Preferably, the solution formulations intended for use in the nose contain 0.38-0.62% olopatadine.

Generally, olopatadine will be added in the form of a pharmaceutically acceptable salt. Examples of the pharmaceutically acceptable salts of olopatadine include inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt. The most preferred form of olopatadine for use in the solution compositions of the present invention is the hydrochloride salt of (Z)-11-(3-dimethylaminopropylidene)-6,11-dihydrodibenz-[b,e]oxepin-2-acetic acid. When olopatadine is added to the compositions of the present invention in this salt form, 0.222% olopatadine hydrochloride is equivalent to 0.2% olopatadine free base, 0.443% olopatadine hydrochloride is equivalent to 0.4% olopatadine free base, and 0.665% olopatadine hydrochloride is equivalent to 0.6% olopatadine free base.

In addition to olopatadine, the aqueous solution compositions of the present invention comprise polyvinylpyrrolidone or polystyrene sulfonic acid in an amount sufficient to enhance the physical stability of the composition. Polyvinylpyrrolidone and polystyrene sulfonic acid are known polymers and both are commercially available from a variety of sources in different grades and in a number of molecular weights. For example, polyvinylpyrrolidone is available in many grades from International Specialty Products (Wayne, N.J.): Plasdone® C-15 (weight avg. MW=8 K), K-26/28 (weight avg. MW=30 K), K-29/32 (weight avg. MW=58 K), K-30 (weight avg. MW=50 K) and K-90 (weight avg. MW=1300 K). Also, polyvinylpyrrolidone is available from BASF Corporation under the Kollidon brand name. As used herein, "polyvinylpyrrolidone" includes homopolymers of vinylpyrrolidone and copolymers of vinylpyrrolidone and vinyl acetate. Vinylpyrrolidone-vinyl acetate copolymers are known as "copovidone" and are commercially available from BASF Corporation as Kollidon VA 64. The polyvinylpyrrolidone ingredient included in the solution compositions of the present invention has a weight average molecular weight of 5000-1,600,000. Most preferred is polyvinylpyrrolidone having a weight average molecular weight of 50,000-60,000. In general, the amount of polyvinylpyrrolidone contained in the compositions of the present invention will be 0.1-3%, preferably 0.2-2%, and most preferably 1.5-2%.

Polystyrene sulfonic acid is commercially available in many grades, including for example the following grades available from Alco Chemical, a division of National Starch & Chemical Company: Versa TL-70 (weight avg. MW=75,000), Versa TL-125 (weight avg. MW=200,000), and Versa TL-502 (weight avg. MW=1,000,000). As used herein, "polystyrene sulfonic acid" includes homopolymers of styrene sulfonic acid and salts, as well as copolymers of styrene sulfonic acid and maleic anhydride. The polystyrene sulfonic acid ingredient included in the solution compositions of the present invention has a weight average molecular weight of 10,000-1,500,000, preferably 75,000 to 1,000,000, and most preferably 75,000. In general, the amount of polystyrene sulfonic acid contained in the compositions of the present invention will be 0.1-1%, preferably 0.15-0.4%, and most preferably 0.25%.

The compositions of the present invention comprise 0.17-0.62% olopatadine and a polymeric physical stability-enhancing ingredient consisting essentially of polyvinylpyrrolidone or polystyrene sulfonic acid in an amount sufficient to enhance the physical stability of the solution. The compositions of the present invention do not contain polyvinyl alcohol, polyvinyl acrylic acid, hydroxypropylmethyl cellulose, sodium carboxymethyl cellulose, xanthan gum or other polymeric physical stability enhancing ingredient.

The compositions of the present invention have a viscosity of 0.5-10 cps, preferably 0.5-5 cps, and most preferably 1-2 cps. This relatively low viscosity insures that the product is comfortable, does not cause blurring, and is easily processed during manufacturing, transfer and filling operations.

In addition to the olopatadine and polyvinylpyrrolidone ingredients, the compositions of the present invention optionally comprise one or more excipients. Excipients commonly used in pharmaceutical compositions intended for topical application to the eyes or nose, such as solutions or sprays, include, but are not limited to, tonicity agents, preservatives, chelating agents, buffering agents, surfactants and antioxidants. Suitable tonicity-adjusting agents include mannitol, sodium chloride, glycerin, sorbitol and the like. Suitable preservatives include p-hydroxybenzoic acid ester, benzalkonium chloride, benzododecinium bromide, polyquaternium-1 and the like. Suitable chelating agents include sodium edetate and the like. Suitable buffering agents include phosphates, borates, citrates, acetates and the like. Suitable surfactants include ionic and nonionic surfactants, though nonionic surfactants are preferred, such as polysorbates, polyethoxylated castor oil derivatives and oxyethylated tertiary octylphenol formaldehyde polymer (tyloxapol). Suitable antioxidants include sulfites, ascorbates, BHA and BHT. The compositions of the present invention optionally comprise an additional active agent. With the exception of the optional preservative ingredient (e.g., polyquaternium-1), the compositions of the present invention preferably do not contain any polymeric ingredient other than polyvinylpyrrolidone or polystyrene sulfonic acid.

Particularly for compositions intended to be administered as eye drops, the compositions preferably contain a tonicity-adjusting agent in an amount sufficient to cause the final composition to have an ophthalmically acceptable osmolality (generally 150-450 mOsm, preferably 250-350 mOsm). The ophthalmic compositions of the present invention preferably have a pH of 4-8, preferably a pH of 6.5-7.5, and most preferably a pH of 6.8-7.2. Compositions of the present invention intended for use in the nose preferably have a pH of 3.5-8. Preferably, compositions intended to be administered to the nose have a pH of 3.5-4.5, and most preferably a pH of 3.8-4.4.

When the compositions of the present invention contain polyvinylpyrrolidone, the polyvinylpyrrolidone ingredient is preferably selected or processed to minimize peroxide content. Freshly produced batches of polyvinylpyrrolidone are preferred over aged batches. Additionally, particularly in cases where the composition will contain greater than 0.5% polyvinylpyrrolidone, the polyvinylpyrrolidone ingredient should be thermally treated (i.e., heated to a temperature above room temperature) prior to mixing with olopatadine in order to reduce the amount of peroxides in the polyvinylpyrrolidone ingredient and minimize the effect of peroxides on the chemical stability of olopatadine. While thermally treating an aqueous solution of polyvinylpyrrolidone for prolonged periods will substantially reduce the amount of peroxides, it can lead to discoloration (yellow to yellowish-brown) of the polyvinylpyrrolidone solution. In order to substantially reduce or eliminate peroxides without discoloring the polyvinylpyrrolidone solution, the pH of the aqueous solution of polyvinylpyrrolidone should be adjusted to pH 11-13 before it is subjected to heat. Much shorter heating times are needed to achieve significant reductions in peroxide levels if the pH of the polyvinylpyrrolidone solution is elevated.

One suitable method of thermally treating the polyvinylpyrrolidone ingredient is as follows. First, dissolve the polyvinylpyrrolidone ingredient in purified water to make a 4-6% solution, then raise the pH of the solution to pH 11-13, preferably 11-11.5, then heat to a temperature in the range of 60-121° C., preferably 65-80° C. and most preferably 70-75° C. The elevated temperature should be maintained for approximately 30-120 minutes (preferably 30 minutes). After the heated solution cools to room temperature, add HCl to adjust the pH to 3.5-8, depending upon the target pH for the olopatadine composition.

The compositions of the present invention are preferably packaged in opaque plastic containers. A preferred container for an ophthalmic product is a low-density polyethylene container that has been sterilized using ethylene oxide instead of gamma-irradiation. A preferred container for a nasal product is a high-density polyethylene container equipped with a nasal spray pump.

Certain embodiments of the invention are illustrated in the following examples.

EXAMPLE 1

Topically Administrable Ophthalmic Solution

| Ingredient | Concentration (% w/v) |
| --- | --- |
| (Z)-11-(3-dimethylaminopropylidene)-6,11-dihydrodibenz[b,e]oxepin-2-acetic acid · HCl ("Olopatadine · HCl") | 0.222* |
| Polyvinylpyrrolidone | 1.6-2.0 |
| Sodium Chloride | 0.55 |
| Benzalkonium Chloride | 0-0.02 |
| Edetate Disodium | 0.01 |
| Dibasic Sodium Phosphate (Anhydrous) | 0.5 |
| NaOH/HCl | q.s. pH 7.0 ± 0.2 |
| Purified Water | q.s. 100 |

*equivalent to 0.2% free base

A representative compounding procedure for the solution composition of this Example is provided below.

Preparation of Polyvinylpyrrolidone Stock Solution

A 4% stock solution of polyvinylpyrrolidone is prepared by dissolving the polyvinylpyrrolidone in purified water, adding NaOH to raise the pH to 11.5, and heating for 30 minutes at 70-75° C. After cooling to room temperature, HCl is added to the stock solution to adjust the pH to 7.

Compounding Procedure

Purified water, dibasic sodium phosphate, sodium chloride, edetate disodium, benzalkonium chloride (as 1% stock solution) and polyvinylpyrrolidone (as 4% stock solution) are added to a container, with mixing after adding each ingredient. NaOH is added to adjust the pH to approximately pH 7, then the drug is added, followed by final pH adjustment to pH 7.0 and the addition of the remaining amount of purified water, with mixing after adding each ingredient. The resulting solution is then filtered through a sterilizing filter and transferred under sterile conditions into ethylene oxide-sterilized LDPE or polypropylene containers.

EXAMPLE 2

Topically Administrable Ophthalmic Solution

| Ingredient | Concentration (% w/v) |
| --- | --- |
| Olopatadine · HCl | 0.222* |
| N-lauroylsarcosine | 0.04 |
| Polystyrene Sulfonic Acid | 0.5 |
| Mannitol | 4.4 |
| Benzalkonium Chloride | 0-0.02 |
| Boric Acid | 0.45 |
| Edetate Disodium | 0.05 |
| Tromethamine | q.s. pH 6.5 ± 0.2 |
| Purified Water | q.s. 100 |

*equivalent to 0.2% free base

A representative compounding procedure for the solution composition of this Example is provided below.

Compounding Procedure

Purified water, mannitol, boric acid, edetate disodium, benzalkonium chloride (as 1% stock solution) and polystyrene sulfonic acid (as a powder) are added to a container, with mixing after adding each ingredient. Tromethamine is added to adjust the pH to approximately pH 6.5, then N-lauroylsarcosine and then the drug is added, followed by final pH adjustment to pH 6.5 and addition of the remaining amount of purified water, with mixing after adding each ingredient. The resulting solution is then filtered through a sterilizing filter and transferred under sterile conditions into ethylene oxide-sterilized LDPE or polypropylene containers.

EXAMPLE 3

Topically Administrable Nasal Solution

| Ingredient | Concentration (% w/v) |
| --- | --- |
| Olopatadine · HCl | 0.222* |
| Polyvinylpyrrolidone | 1.6-2.0 |
| Sodium Chloride | 0.3-0.6 |
| Benzalkonium Chloride | 0-0.02 |
| Edetate Disodium | 0.01 |
| Dibasic Sodium Phosphate (Anhydrous) | 0.5 |
| NaOH/HCl | q.s. pH 3.8-7 |
| Purified Water | q.s. 100 |

*equivalent to 0.2% free base

A representative compounding procedure for the solution composition of this Example is provided below.

Preparation of Polyvinylpyrrolidone Stock Solution

A 4% stock solution of polyvinylpyrrolidone is prepared by dissolving the polyvinylpyrrolidone in purified water, adding NaOH to raise the pH to 11.5, and heating for 30 minutes at 70-75° C. After cooling to room temperature, HCl is added to the stock solution to adjust the pH to 7.

Compounding Procedure

Purified water, dibasic sodium phosphate, sodium chloride, edetate disodium, benzalkonium chloride (as 1% stock solution), polyvinylpyrrolidone (as 4% stock solution), and the drug are added to a container, with mixing after adding each ingredient. NaOH/HCl is added to adjust the pH to approximately pH 4, and the remaining amount of purified water is added. The resulting solution is then filtered through a sterilizing filter and aseptically transferred into high-density polyethylene, spray-pump containers.

EXAMPLE 4

Topically Administrable Nasal Solution

| Ingredient | Concentration (% w/v) |
| --- | --- |
| Olopatadine · HCl | 0.443* |
| Polyvinylpyrrolidone | 1.6-2.0 |
| Sodium Chloride | 0.3-0.6 |
| Benzalkonium Chloride | 0.01 + 3% xs |
| Edetate Disodium | 0.01 |

-continued

| Ingredient | Concentration (% w/v) |
|---|---|
| Dibasic Sodium Phosphate (Anhydrous) | 0.5 |
| NaOH/HCl | q.s. pH 3.8-4.4 |
| Purified Water | q.s. 100 |

*equivalent to 0.4% free base

The solution composition of this Example may be prepared using the procedure described above for the solution composition of Example 3.

EXAMPLE 5

The compositions shown in Table 1 below were prepared and subjected to stability studies. In no case was the polymeric ingredient autoclaved and none of the compositions was filtered through a 0.2 μm filter. One set of samples (two vials each) of each of the compositions was subjected to three refrigeration—room temperature cycles and a second set (two vials each) was subjected to continuous low-temperature exposure. The results are shown in Table 2 below.

TABLE 1

| | FORMULATION | | | | | | |
|---|---|---|---|---|---|---|---|
| | A | B | C | D | E | F | G |
| INGREDIENT | Concentration (% w/w) | | | | | | |
| Olopatadine.HCl | 0.222 | 0.222 | 0.222 | 0.222 | 0.222 | 0.222 | 0.222 |
| Polyvinyl Alcohol (Airvol 2055) | 0.1 | — | — | — | — | — | — |
| Hydroxypropyl Methylcellulose (2910) | — | 0.05 | — | — | — | — | — |
| Xanthan Gum (AR) | — | — | 0.02 | — | — | — | — |
| Carbopol 974P | — | — | — | 0.01 | — | — | — |
| Polyvinyl pyrrolidone (wt. Avg. MW = 58K) | — | — | — | — | 1.0 | 1.8 | — |
| Sodium Carboxymethyl-cellulose (762P) | — | — | — | — | — | — | 0.1 |
| Benzalkonium Chloride | 0.01 + 1% xs | 0.01 + 1% xs | 0.01 + 1% xs | 0.01 + 1% xs | 0.01 + 1% xs | 0.01 + 1% xs | 0.01 + 1% xs |
| Sodium Chloride | 0.6 | 0.6 | 0.6 | 0.6 | 0.6 | 0.6 | 0.6 |
| Dibasic Sodium Phosphate (anhydrous) | 0.5 | 0.5 | 0.5 | 0.5 | 0.5 | 0.5 | 0.5 |
| NaOH/HCl | q.s. pH 7 | q.s. pH 7 | q.s. pH 7 | q.s. pH 7 | q.s. pH 7 | q.s. pH 7 | q.s. pH 7 |
| Purified Water | q.s. 100 | q.s. 100 | q.s. 100 | q.s. 100 | q.s. 100 | q.s. 100 | q.s. 100 |
| Viscosity* (cps) | 1.02 | 1.40 | 1.42 | 0.97 | 1.20 | 1.45 | 1.16 |

*Brookfield viscometer (60 RPM, CP-42)

TABLE 2

| | Refrigeration - RT cycles | | Continuous low-temperature exposure | | |
|---|---|---|---|---|---|
| Formulation | One cycle | Three cycles | Day 7 | Day 14 | Day 28 |
| A | Clear, no particles | Clear, few particles (one vial) | Clear, few particles | Clear, fiber-like particles | Clear, particles |
| B | Clear, no particles | Clear, a crystal (2 mm) observed in one vial | Clear, particles and crystals | Clear, crystals and fiber-like particles | Clear, crystals |
| C | Clear, no particles | Clear, crystals | Clear, crystals | Clear, crystals | Clear, crystals |
| D | Clear, lots of crystals | Clear, lots of crystals | Clear, lots of crystals | Clear, lots of crystals | Clear, crystals |
| E | Clear, no particles | Clear, no particles | Clear, no particles | Clear, no particles | Clear, no particles |
| F | Clear, no particles | Clear, no particles | Clear, no particles | Clear, no particles | Clear, no particles |
| G | Clear, no particles | Clear, crystals | Clear, crystals | Clear, crystals | Clear, crystals |

EXAMPLE 6

The compositions shown in Table 3 below were subjected to freeze-thaw stability studies at two conditions (with and without seed; seed=0-½ Canyon pumice (from Charles B. Chrystal Co., Inc., New York, N.Y.) at 1 mg in 5 mL of formulation) and two temperatures (0° C. or −20° C.). In no case was the polymeric ingredient autoclaved and none of the compositions was filtered through a 0.2 μm filter. Each of the compositions (two vials each) was subjected to six freeze-thaw cycles where one cycle was three days at low temperature (i.e., either 0° C. or −20° C.), followed by one day at uncontrolled room temperature. The compositions were visually inspected and the results recorded. The results are shown in Table 4 below.

TABLE 3

| Ingredient | FORMULATION | | |
|---|---|---|---|
| | H | I | J |
| | Concentration (% w/w) | | |
| Olopatadine · HCl | 0.222 | 0.222 | 0.222 |
| Benzalkonium Chloride | 0.01 + 3% xs | 0.01 + 3% xs | 0.01 + 3% xs |
| Edetate Disodium | 0.01 | 0.01 | 0.01 |
| Hydroxypropyl methylcellulose | 1.8 | — | — |
| Carbopol 974P | — | 0.6 | — |
| Polyvinyl alcohol (Airvol 205S) | — | — | 1.8 |
| Sodium Chloride | 0.55 | 0.55 | 0.55 |
| Dibasic Sodium Phosphate (Anhydrous) | 0.5 | 0.5 | 0.5 |
| NaOH/HCl | Adjust pH 7.0 ± 0.2 | Adjust pH 7.0 ± 0.2 | Adjust pH 7.0 ± 0.2 |
| Purified Water | QS to 100% | QS to 100% | QS to 100% |

TABLE 4

| FORMULATION | OBSERVATION |
|---|---|
| H | No precipitation after 6 cycles with or without seed at either temperature |
| I | Hazy from 1st cycle onward with or without seed at both temperatures |
| J | No precipitation after 6 cycles with or without seed at either temperature |

EXAMPLE 7

The compositions shown in Table 5 below were subjected to freeze-thaw stability studies at two conditions (with and without seed; seed=same as in Example 4 above) and two temperatures (0° C. or −20° C.). In no case was the polymeric ingredient autoclaved and none of the compositions was filtered through a 0.2 μm filter. Each of the compositions (three vials each) was subjected to up to six freeze-thaw cycles where one cycle was three days at low temperature (i.e., either 0° C. or −20° C.), followed by one day at uncontrolled room temperature. The compositions were visually inspected and the results recorded. The results are shown in Table 6 below.

TABLE 5

| INGREDIENT | FORMULATION | | | | | | | | |
|---|---|---|---|---|---|---|---|---|---|
| | K | L | M | N | O | P | Q | R | S |
| | Concentration (% w/w) | | | | | | | | |
| Olopatadine.HCl | 0.222 | 0.222 | 0.222 | 0.222 | 0.222 | 0.222 | 0.333 | 0.333 | 0.333 |
| Polyvinyl pyrrolidone (wt. Avg. MW = 58K) | 2 | 2 | — | 1.8 | — | — | 2 | 2 | — |
| Polyethylene Glycol (400) | — | 2 | 2 | — | — | — | — | 2 | — |
| Polyvinyl pyrrolidone (wt. avg. MW = 1300K) | — | — | — | — | 1.8 | — | — | — | 2 |
| Benzalkonium Chloride | 0.01 + 3% xs | 0.01 | 0.01 + 3% xs | 0.01 + 3% xs | 0.01 + 3% xs | 0.01 + 3% xs | 0.01 + 3% xs | 0.01 | 0.01 |
| Dibasic Sodium Phosphate (Anhydrous) | 0.5 | 0.5 | 0.5 | 0.5 | 0.5 | 0.5 | 0.5 | 0.5 | 0.5 |
| Sodium Chloride | 0.55 | 0.3 | 0.3 | 0.55 | 0.55 | 0.6 | 0.55 | 0.3 | 0.3 |
| Edetate Disodium | 0.02 | 0.01 | 0.01 | 0.02 | 0.02 | — | 0.02 | 0.01 | 0.01 |
| NaOH/HCl | q.s. pH 7 | q.s. pH 7 | q.s. pH 7 | q.s. pH 7 | q.s. PH 7 | q.s. pH 7 | q.s. pH 7 | q.s. pH 7 | q.s. pH 7 |
| Purified Water | q.s. 100 | q.s. 100 | q.s. 100 | q.s. 100 | q.s. 100 | q.s. 100 | q.s. 100 | q.s. 100 | q.s. 100 |

TABLE 6

| Formulation | # cycles | Observation (No. of vials showing precipitation) | | | |
|---|---|---|---|---|---|
| | | Seed 0° C. | Seed −20° C. | No Seed 0° C. | No Seed −20° C. |
| K | 6 | 0/3 | 0/3 | 0/3 | 0/3 |
| L | 6 | 0/3 | 0/3 | 0/3 | 0/3 |
| M | 6 | 0/3 | 0/3 | 0/3 | 0/3 |
| N | 6 | 0/3 | 0/3 | 0/3 | 0/3 |
| O | 6 | 0/3 | 0/3 | 0/3 | 0/3 |
| P | 5 | 1/3 | 0/3 (6 cycles) | 2/3 | 2/3 (6 cycles) |
| Q | 5 | 3/3 | 0/3 (6 cycles) | 3/3 | 0/3 (6 cycles) |
| R | 6 | 0/3 | 0/3 | 0/3 | 0/3 |
| S | 5 | 3/3 | 3/3 (3 cycles) | 3/3 | 2/3 (3 cycles) |

EXAMPLE 8

The formulations shown in Table 7 were prepared and subjected to freeze-thaw testing for 5.5 cycles. For one set of samples, one cycle was defined as one week at 0° C. followed by one week at uncontrolled room temperature (approx. 21° C.). For another set of samples, one cycle was defined as one week at −20° C. followed by one week at uncontrolled room temperature (approx. 21° C.). The results are shown in Table 8.

TABLE 7

| | FORMULATION | |
|---|---|---|
| | T | U |
| INGREDIENT | Concentration (% w/w) | |
| Olopatadine · HCl | 0.222 | 0.222 |
| Polystyrene Sulfonic Acid (Wt. Avg. MW = 1000K) | 0.25 | 0.5 |
| Benzalkonium Chloride | 0.01 | 0.01 |
| Edetate Disodium | 0.05 | 0.05 |
| Mannitol | 4.4 | 4.4 |
| Boric Acid | 0.45 | 0.45 |
| N-lauroylsarcosine | 0.04 | 0.04 |
| Tromethamine/HCl | q.s. pH 6.5 | q.s. pH 6.5 |
| Purified Water | q.s. 100 | q.s. 100 |

TABLE 8

| FORMULATION | OBSERVATION |
|---|---|
| T | No precipitation at either temperature |
| U | No precipitation at either temperature |

EXAMPLE 9

Seven compositions were prepared and subjected to freeze-thaw stability studies. Each of the seven compositions contained purified water, 0.222% (w/w) Olopatadine HCl, 0.01% (w//w) (+3% excess) benzalkonium chloride, 0.06% (w/w) sodium chloride 0.5% (w/w) dibasic sodium phosphate, and NaOH/HCl to adjust pH to 7. The seven samples were differentiated by their amount or grade (molecular weight) of polyvinylpyrrolidone ingredient, as shown in Table 9. In no case was the polymeric ingredient autoclaved and the compositions were filtered through a 0.2 μm filter. The seven samples were placed in scintillation vials containing stir bars and were subjected to freeze-thaw stability studies at two conditions and two temperatures (3-4° C. or −21° C.). After six cycles of 3 days at low temperature and one day at room temperature (with stirring), the samples were subjected to 3.5 cycles of one week at low temperature, followed by one week at room temperature (no stirring). Although fibers were observed in a few samples during the study, no crystals were observed in any samples until the end of the study. At the end of the study, the stir bars were removed and the samples (replicate samples of each composition) were visually inspected. The results are shown in Table 9.

TABLE 9

| Sample | Polyvinylpyrrolidone (w/w); wt. avg. MW) | Particulates | Fibers/ Amorphous particles | Clarity |
|---|---|---|---|---|
| Refrigeration Condition (3-4° C.) | | | | |
| 9.1A | None | None | Fibers | Clear |
| 9.1B | None | Crystals | Amorphous Particles | Hazy |
| 9.2A | 0.01% (58K) | None | Fibers | Clear |
| 9.2B | 0.01% (58K) | None | Fibers | Clear |
| 9.3A | 0.1% (58K) | None | Maybe fibers | Clear |
| 9.3B | 0.1% (58K) | None | None | Clear |
| 9.4A | 0.2% (58K) | None | None | Clear |
| 9.4B | 0.2% (58K) | None | None | Clear |
| 9.5A | 0.5% (58K) | None | None | Clear |
| 9.5B | 0.5% (58K) | None | None | Clear |
| 9.6A | 1.0% (58K) | None | None | Clear |
| 9.6B | 1.0% (58K) | None | None | Clear |
| 9.7A | 0.1% (1300K) | Big Particles | Fibers | Clear |
| 9.7B | 0.1% (1300K) | Particles | Fibers | Clear |
| Freeze-Thaw Condition (−21° C.) | | | | |
| 9.1A | None | None | Fibers | Clear |
| 9.1B | None | None | Fibers | Clear |
| 9.2A | 0.01% (58K) | None | Fibers | Clear |
| 9.2B | 0.01% (58K) | None | Fibers | Clear |
| 9.3A | 0.1% (58K) | None | None | Clear |
| 9.3B | 0.1% (58K) | None | None | Clear |
| 9.4A | 0.2% (58K) | None | None | Clear |
| 9.4B | 0.2% (58K) | None | None | Clear |
| 9.5A | 0.5% (58K) | None | None | Clear |
| 9.5B | 0.5% (58K) | None | None | Clear |
| 9.6A | 1.0% (58K) | None | None | Clear |
| 9.6B | 1.0% (58K) | None | None | Clear |
| 9.7A | 0.1% (1300K) | None | None | Clear |
| 9.7B | 0.1% (1300K) | None | None | Clear |

EXAMPLE 10

The formulations shown in Table 10 were prepared and subjected to thermal cycling studies and short-term stability studies. For the cycling studies, each cycle consisted of 2 days at the first temperature, then two days at the second temperature (4 days total). Cycles were repeated three times. Each sample was run in triplicate. The short-term stability studies were conducted at two conditions: 4° C. and 25° C. The results of these studies are shown in Table 11.

TABLE 10

| Component | % w/w | | | | | |
|---|---|---|---|---|---|---|
| | V | W | X | Y | Z | AA |
| Olopatadine.HCl | 0.222 | 0.443 | 0.665 | 0.222 | 0.443 | 0.665 |
| Polyvinyl-pyrrolidone (wt. avg. MW = 58K) | 1.8 | 1.8 | 1.8 | 0 | 0 | 0 |
| Benzalkonium Chloride | 0.01 + 3% xs | 0.01 + 3% xs | 0.01 + 3% xs | 0.01 + 3% xs | 0.01 + 3% xs | 0.01 + 3% xs |
| Edetate Disodium | 0.01 | 0.01 | 0.01 | 0.01 | 0.01 | 0.01 |
| Sodium Chloride | 0.55 | 0.55 | 0.55 | 0.55 | 0.55 | 0.55 |
| Dibasic Sodium Phosphate (Anhydrous) | 0.5 | 0.5 | 0.5 | 0.5 | 0.5 | 0.5 |
| NaoH/HCl | qs pH 4.2 ± 0.2 | qs pH 4.2 ± 0.2 | qs pH 4.2 ± 0.2 | qs pH 4.2 ± 0.2 | qs pH 4.2 ± 0.2 | qs pH 4.2 ± 0.2 |
| Purified Water | Qs 100 | qs 100 | qs 100 | qs 100 | qs 100 | qs 100 |

TABLE 11

| Storage Condition | Age | FORMULATION | | | | | |
|---|---|---|---|---|---|---|---|
| | | V (0.2%, w/PVP) | W (0.4%, w/PVP) | X (0.6%, w/PVP) | Y (0.2% w/o PVP) | Z (0.4% w/o PVP) | AA (0.6% w/o PVP) |
| | Initial | √ | √ | √ | √ | √ | √ |
| Cycle −18° C. to 25° C. | 4 days | √ | √ | √ | √ | √ | √ |
| | 8 days | √ | √ | √ | √ | √ | √ |
| | 12 days | √ | √ | √ | √ | √ | √ |
| Cycle 4° C. to 25° C. | 4 days | √ | √ | √ | √ | √ | √ |
| | 8 days | √ | √ | √ | √ | √ | √ |
| | 12 days | √ | √ | √ | √ | √ | √ |
| 4° C. | 4 days | √ | √ | √ | √ | √ | √ |
| | 8 days | √ | √ | √ | √ | √ | √ |
| | 12 days | √ | √ | √ | √ | √ | √ |
| | 4 weeks | √ | √ | Ppt* | √ | Ppt | Ppt |
| | 8 weeks | √ | √ | Ppt | √ | Ppt | Ppt |
| | 12 weeks | √ | √ | Ppt | √ | Ppt | Ppt |
| | 16 weeks | √ | √ | Ppt | √ | Ppt | Ppt |
| 25° C. | 4 days | √ | √ | √ | √ | √ | √ |
| | 8 days | √ | √ | √ | √ | √ | √ |
| | 12 days | √ | √ | √ | √ | √ | √ |
| | 4 weeks | √ | √ | √ | √ | √ | Ppt |
| | 8 weeks | √ | √ | √ | √ | √ | Ppt |
| | 12 weeks | √ | √ | √ | √ | Ppt | Ppt |
| | 16 weeks | √ | √ | √ | √ | Ppt | Ppt |

√ = Clear, Colorless;
Ppt = precipitate observed in 3 of 3 samples;
*Precipitate observed in 2 of 3 samples (Formulation X, 4° C., 4 weeks)

EXAMPLE 11

The formulations shown in Table 12 were prepared and stored at the indicated temperature (RT=room temperature: approximately 25±4° C.; Refrigerated=approximately 3±2° C.). Observations were made at the indicated time points. The results are shown in Table 13.

TABLE 12

| INGREDIENT | FORMULATION | | |
|---|---|---|---|
| | AB | AC | AD |
| | Concentration (% w/w) | | |
| Olopatadine · HCl | 0.222 | 0.443 | 0.665 |
| Polyvinylpyrrolidone (wt. avg. MW = 58K) | 1.8 | 1.8 | 1.8 |

TABLE 12-continued

| INGREDIENT | FORMULATION | | |
|---|---|---|---|
| | AB | AC | AD |
| | Concentration (% w/w) | | |
| Benzalkonium Chloride | 0.01 + 3% xs | 0.01 + 3% xs | 0.01 + 3% xs |
| Edetate Disodium | 0.01 | 0.01 | 0.01 |
| Sodium Chloride | 0.36 | 0.35 | 0.33 |
| Dibasic Sodium Phosphate (Anhydrous) | 0.5 | 0.5 | 0.5 |
| NaoH/HCl | qs pH 4.0 ± 0.2 | qs pH 4.0 ± 0.2 | qs pH 4.0 ± 0.2 |
| Purified Water | qs 100 | qs 100 | qs 100 |

TABLE 13

| Storage Condition | Age/Time Pull | Formulation AB | Formulation AC | Formulation AD |
|---|---|---|---|---|
| RT | 1 month | Clear | Clear | Clear |
|  | 2 month | Clear | Clear | Clear |
|  | 3 month | Clear | Clear | Clear |
|  | 4 month | Clear | Clear | Clear |
| Refrigerated | 1 month | Clear | Clear | Clear |
|  | 2 month | Clear | Clear | Clear |
|  | 3 month | Clear | Clear | Clear |
|  | 4 month | Clear | Clear | Clear |

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A topically administrable solution composition for treating allergic or inflammatory disorders of the eye and nose, wherein the solution has a pH from 6.5-7.5 and a viscosity of 1-2 cps, and wherein the solution consists essentially of:
   a) 0.18-0.22% (w/v) olopatadine;
   b) 1.5-2% (w/v) polyvinylpyrrolidone having a weight average molecular weight of 50,000-60,000;
   c) a preservative selected from the group consisting of benzalkonium chloride; benzododecinum bromide; and polyquaternium-1;
   d) edetate disodium;
   e) a tonicity-adjusting agent selected from the group consisting of mannitol and sodium chloride;
   f) a buffering agent selected from the group consisting of phosphates and borates;
   g) optionally a pH-adjusting agent selected from the group consisting of NaOH and HCl; and
   h) water.

* * * * *